(12) United States Patent
Doursounian et al.

(10) Patent No.: US 6,527,809 B1
(45) Date of Patent: Mar. 4, 2003

(54) TRIAL ACETABULUM OR IMPLANTABLE ACETABULUM WITH ADJUSTABLE ORIENTATION

(76) Inventors: Lévon Doursounian, 15 avenue Victor Hugo, 75116 Paris (FR); Michel Porte, 46, rue du Pr. Langevin, 93150 Le Blanc-Mesnil (FR)

( * ) Notice: Subject to any disclaimer, the term of this patent is extended or adjusted under 35 U.S.C. 154(b) by 0 days.

(21) Appl. No.: 09/763,212
(22) PCT Filed: Aug. 16, 1999
(86) PCT No.: PCT/FR99/01994
§ 371 (c)(1),
(2), (4) Date: Mar. 29, 2001
(87) PCT Pub. No.: WO00/09045
PCT Pub. Date: Feb. 24, 2000

(30) Foreign Application Priority Data

Aug. 17, 1998 (FR) .............................. 98 10473

(51) Int. Cl.⁷ .............................. A61F 2/32; A61F 2/34
(52) U.S. Cl. ................................. 623/22.28; 623/22.25
(58) Field of Search ........................... 623/22.17, 22.19, 623/22.24–22.29, 19.12

(56) References Cited

U.S. PATENT DOCUMENTS

| 5,480,442 | A | * | 1/1996 | Bertagnoli | ............... | 623/17 |
| 5,454,230 | A | | 8/1996 | Kinsinger et al. | | |
| 5,549,696 | A | * | 8/1996 | Willi | .................... | 623/22 |
| 5,609,648 | A | * | 3/1997 | Oehy et al. | ............... | 623/22 |
| 5,645,607 | A | | 7/1997 | Hickey | | |
| 5,938,702 | A | * | 8/1999 | Lopez et al. | ............... | 623/22 |

FOREIGN PATENT DOCUMENTS

| DE | 195 21 147 C1 | 12/1996 |
| EP | 0 327 509 | 8/1989 |
| EP | 0 445 068 | 9/1991 |
| EP | 0 612 509 A3 | 8/1994 |
| EP | 0 612 509 A2 | 8/1994 |
| EP | 0 630 625 A2 | 12/1994 |
| EP | 0 630 625 A3 | 12/1994 |
| EP | 0 640 326 A1 | 3/1995 |
| EP | 0 793 949 A1 | 9/1997 |
| EP | 0 807 426 A2 | 11/1997 |
| WO | WO 86/05384 | 9/1986 |

* cited by examiner

Primary Examiner—David H. Willse
Assistant Examiner—Javier G. Blanco
(74) Attorney, Agent, or Firm—Young & Thompson

(57) ABSTRACT

An acetabular cup includes a hemispheric acetabular shell designed to be set in a cotyloid cavity and a hemispheric insert made of biocompatible plastic material and designed to be engaged concentrically in the acetabular shell. An external base is provided with studs for anchoring in the cotyloid cavity bone and designed to receive the acetabular shell. An internal cup is designed to be placed in the acetabular cup opposite the external base and elements for linking the external base and the internal cup. The base and the cup define elements for adjusting the acetabular cup angular position in the cotyloid cavity according to the orientation to be given to the articulation while the elements linking the external base to the internal cup comprise elements for blocking the acetabular cup with respect to the external base after the acetabular cup angular position has been adjusted.

9 Claims, 2 Drawing Sheets

TRIAL ACETABULUM OR IMPLANTABLE ACETABULUM WITH ADJUSTABLE ORIENTATION

CROSS REFERENCE TO RELATED APPLICATION

This is the 35 USC 371 national stage of international application PCT/FR99/01994 filed on Aug. 16, 1999, which designated the United States of America.

FIELD OF THE INVENTION

The present invention concerns total hip prostheses and relates more particularly to prostheses which require fitting of a device intended to restore an acetabular cavity of the iliac bone which has been damaged, in particular due to arthrosis, with a view to being able to receive the head of a femoral prosthesis.

BACKGROUND OF THE INVENTION

In order to restore an acetabular cavity, it is customary to put a prosthetic acetabulum in place and to fix it either by cement or by impaction or with the aid of suitable screws.

However, exact orientation of the acetabulum to be implanted in the acetabular cavity as a function of the orientation of the joint to be restored is very delicate insofar as the anatomical references are not reliable.

This entails risks of error in the orientation of the acetabulum, and these can lead to poor orientation of the prosthetic joint, with risks of luxation of the prosthesis.

SUMMARY OF THE INVENTION

The invention aims to remedy the disadvantages of the prior art by making available an implantable acetabulum with which it is possible to choose a correct orientation of the prosthetic acetabular cavity.

The subject of the invention is therefore a trial acetabulum or implantable acetabulum comprising a hemispherical cup intended to be placed in an acetabular cavity, and a hemispherical insert of biocompatible plastic intended to be engaged concentrically in said cup, characterized in that it additionally comprises an external cap in the form of a spherical dish provided with pins for anchoring in the bone of the acetabular cavity and intended to receive the cup, an internal plate intended to be placed in the cup opposite the external cap and connection means for connecting the external cap and the internal plate, the cap and the plate defining means for adjusting the angular position of the cup in the acetabular cavity as a function of the orientation to be given to the joint, while the means for connecting the external cap to the internal plate include means for immobilizing the cup relative to the external cap after the angular position of said cup has been adjusted.

According to other characteristics of the invention:

- the external cap includes a threaded centering sleeve, which protrudes inward and is intended to cooperate with an external centering collar provided on the internal plate, the sleeve and the collar guiding the translational movement of the internal plate relative to the external cap, a tightening screw which is intended to be engaged in the threaded sleeve of the external cap and whose frustoconical head cooperates with a seat of corresponding shape formed in the internal plate and coaxial to said collar forming, with the threaded sleeve of the external cap and the collar of the internal plate, said means for connecting the cap to the plate;

- the hemispherical cup includes a central orifice traversed by the means for connecting the external cap to the internal plate, with a clearance which allows the angular position of the cup to be adjusted relative to the cap in all directions;

- the hemispherical insert is a trial insert which includes a central orifice for access to the screw for connecting the external cap to the internal plate;

- the insert is a complete and final hemispherical insert which can replace the trial insert upon completion of the operation of orienting and immobilizing the cup relative to the external cap;

- the cup comprises an external zone of reduced thickness for receiving the external cap in such a way as to present, together with the external cap, an almost continuous external surface;

- the cup has, in its internal wall, a thinned wall portion receiving the internal plate;

- the angular extent of the external zone receiving the external cap and the angular extent of the internal wall portion receiving the internal plate are greater than the angular extents of the cap and of the plate by a value corresponding at least to the variation to obtain in the angular orientation of the cup relative to the external cap and to the internal plate.

- the head of the screw has a concave end surface, while the summit of the final insert has a recess which is intended to prevent the summit of said insert from abutting against the head of the screw.

BRIEF DESCRIPTION OF THE DRAWINGS

The invention will be better understood from the following description which is given solely by way of example and in which reference is made to the attached drawings, in which.

DETAILED DESCRIPTION OF THE INVENTION

Figure 1:
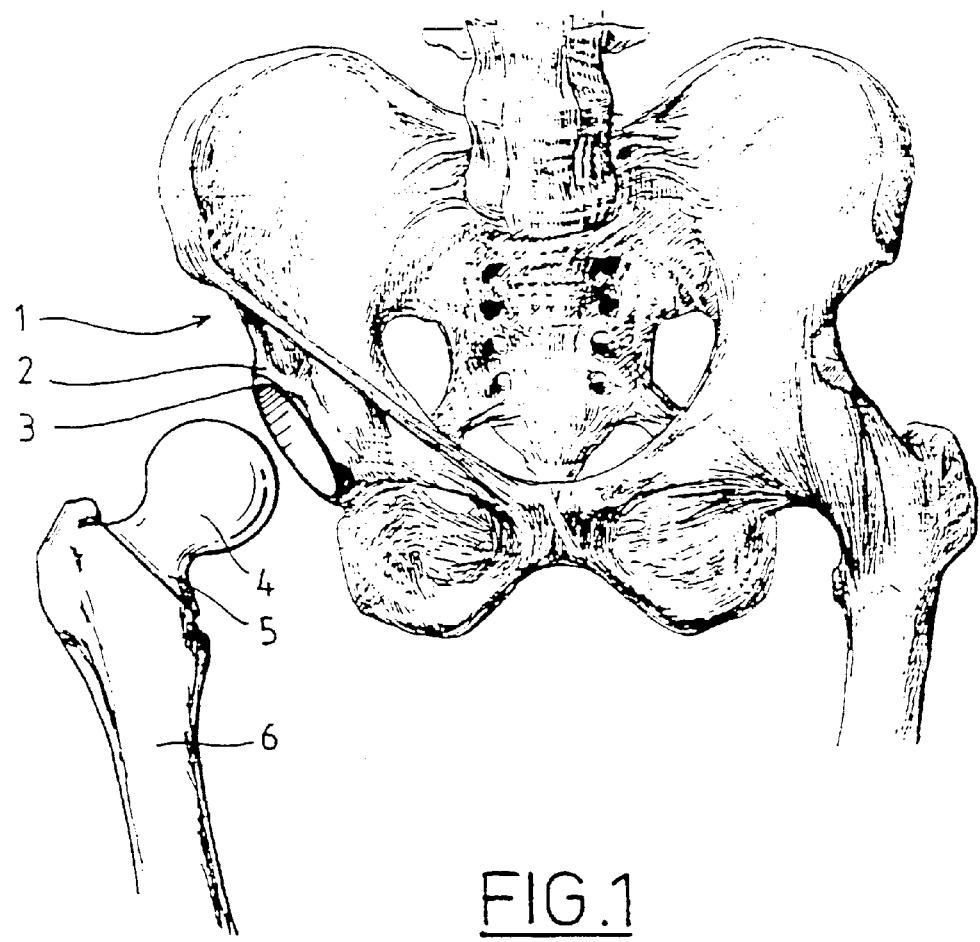
FIG. 1 is a diagrammatic view of a portion of the human skeleton which is intended to receive a hip prosthesis comprising an element for restoring the acetabular cavity.

The pelvic bones of a human skeleton are represented in FIG. 1, in particular the iliac bone 1, the acetabular cavity 2 of the latter having an implanted acetabulum 3 which is in turn intended to receive the head 4 of a femoral prosthesis 5 fixed to the diaphysis of a femur 6.

Figure 2:
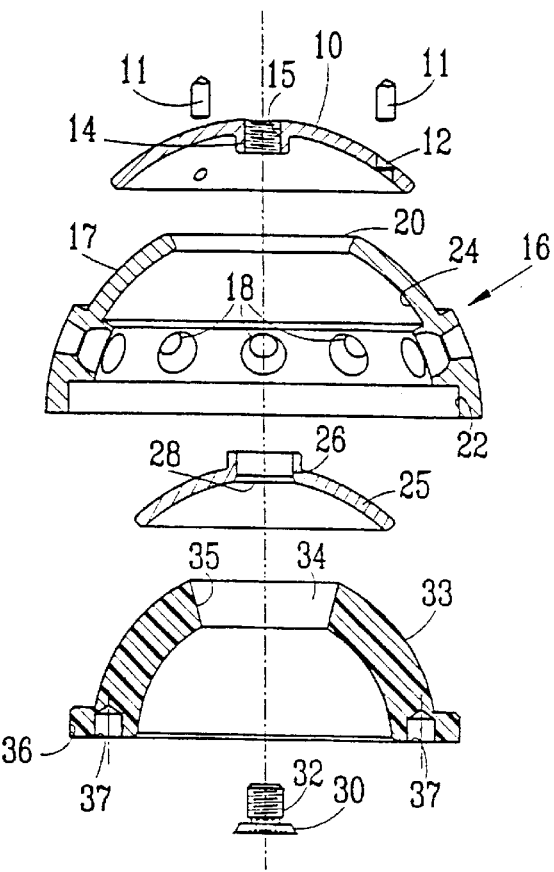
FIG. 2 is an exploded sectional view of an implantable acetabulum according to the invention.

The implantable acetabulum according to the invention is shown in FIG. 2.

It essentially comprises an external cap 10 in the form of a spherical dish and is provided externally with anchoring fingers 11 arranged at 120° about its summit and fixed, for example by welding, in indents 12 formed in the external surface of the cap.

The external cap 10 comprises a threaded axial sleeve 14 which protrudes inward and has a lower thread 15.

The acetabulum additionally comprises a hemispherical cup 16 which has, in its zone of contact with the external cap 10, a region 17 of reduced thickness intended to absorb the thickness of the external cap 10 in such a way as to present, together with said external cap, an almost continuous external surface.

It will be noted, however, that the zone of reduced thickness 17 of the cup 16 has a greater angular extent than that of the external cap 10 so as to permit angular adjustment of the cup relative to the cap.

The cup 16 additionally comprises a series of peripheral holes 18 which are intended to receive screws (not shown) for fixing the acetabulum in the acetabular cavity.

The cup 16 comprises a central orifice 20 permitting its angular orientation relative to the external cap 10, but without going beyond the edges of said cap.

On its side of greater diameter, the cup 16 has a bore 22 which is intended to receive the shoulder, of corresponding shape, of an insert which will be described below.

Formed in the internal wall of the cup 16, in the zone of the latter extending between the fixing holes 18 and the central orifice 20, there is a thinned wall portion 24 for receiving an internal plate 25 which is also in the form of a spherical dish and comprises a central collar 26 protruding outward and intended to cooperate with the central sleeve 14 of the external cap 10 in order to center the internal plate 25 relative to the external cap 10 and to ensure their relative displacement in translation in a manner which will be described below.

Formed in the internal wall of the internal plate 25 there is a frustoconical seat 28 coaxial to the collar 26 and receiving the frustoconical head 30 of a screw 32, intended to cooperate with the internal thread 15 of the sleeve 14 of the external cap 10.

The implantable acetabulum additionally comprises a trial insert 33 of biocompatible plastic, for example of polyoxymethylene, polycarbonate or polyethylene.

The insert 33 is of a hemispherical shape adapted to the internal volume of the cup 16 and has a central orifice 34 with frustoconical wall 35 intended to permit access to the connecting screw 32 during the operations of adjusting the orientation of the cup 16 relative to the external cap 10.

Moreover, the insert 33 comprises a peripheral shoulder 36 which is intended to be received in the bore 22 of the cup 16.

Finally, the insert 33 has two grip holes 37 intended to receive the lugs of a gripping instrument which is designed to place the insert 33 in the cup 16 and to remove it from this cup.

Figure 3:
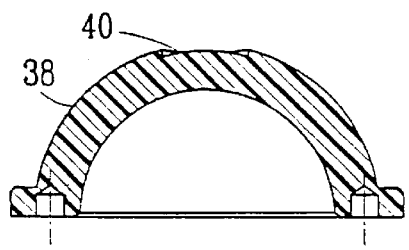
FIG. 3 is a sectional view of a final insert to be placed in the cup of the acetabulum in FIG. 2.

As has been mentioned above, the insert 33 is a trial insert made of polyoxymethylene resistant to multiple sterilization. It can be replaced by a final insert 38 which is shown in FIG. 3 and whose construction is identical to that of the trial insert 33, but whose surface is a solid hemispherical surface.

The final insert is made of a more flexible material, such as polyethylene.

Figure 2A:
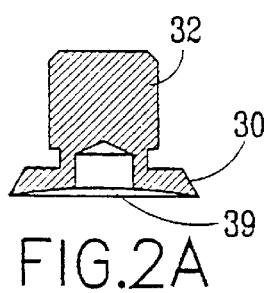
FIG. 2A is a sectional view, on an enlarged scale, of the connecting screw used in the construction of the acetabulum in FIG. 2.

As can be better seen in FIG. 2A, the head 30 of the screw 32 has a concave end surface 39, while the summit of the final insert 38 also has a recess 40 intended to prevent the summit of the final insert 38 from abutting against the head 30 of the screw 32.

Figure 4:
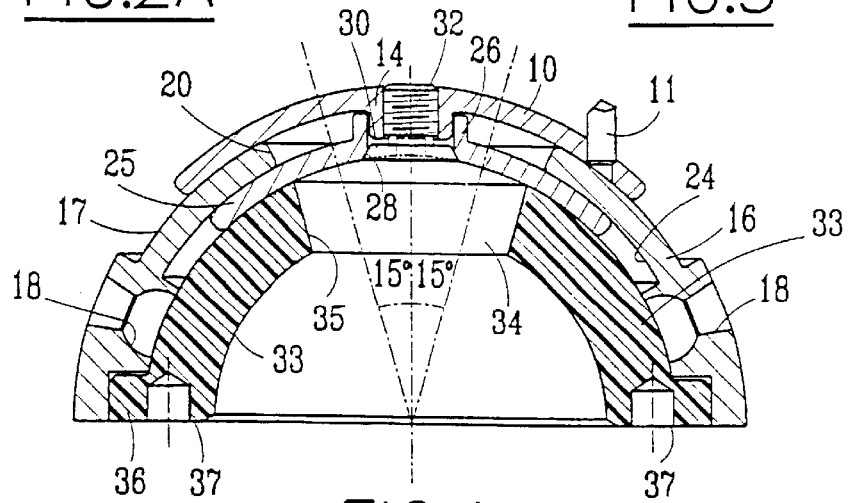
FIG. 4 is a sectional view, on an enlarged scale, of the implantable acetabulum according to the invention in the assembled state.

In FIG. 4, the acetabulum according to the invention has been represented in the assembled position.

The external cap 10 provided with these anchoring fingers 11 is assumed to be fitted by impaction in an acetabular cavity (not shown).

The cup 16 placed against the external cap 10 is maintained assembled to the latter by the internal plate 25 whose external collar 26 is engaged on the threaded sleeve 14 of the external cap 10.

The connection between the external cap 10 and the internal plate 25 is provided by the screw 32 whose frustoconical head 30 cooperates with the seat 28 of complementary shape of the internal plate 25.

Formed between the external cap 10 and the internal plate 25 there is a space which permits angular orientation of the cup 16 relative to the external cap 10 in all directions.

To this end, the diameter of the central orifice 20 of the cup 16 is such that the cup 16 can be displaced angularly relative to the assembly made up of the external cap 10 and the internal plate 25, by an angle of for example 15° either side of its central position shown in FIG. 3.

To this end, the angular extent of the zones of lesser thickness 17 and 24 formed in the external and internal walls of the cup 16 is greater by a value corresponding to the angular extents of the external cap 10 and of the internal plate 25.

It will thus be appreciated that after the cup 16 has been placed between the external cap 10 and the internal plate 25, it is possible to displace the cup 16 angularly in all directions between the cap 10 and the plate 25. In order to adjust the orientation of the cup as a function of the orientation to be given to the joint which is to be restored, the trial insert 33 is placed in the cup 16. Then, a customary apparatus for adjusting the orientation of the acetabulum (not shown), called an acetabulum support, is introduced into the trial insert, and one then proceeds to adjust the orientation of the joint by displacing the assembly formed by the cup 16 and the trial insert 33 relative to the external cap 10 and to the internal plate 25.

When the correct orientation is determined, the adjustment apparatus is withdrawn and the cup 16 is immobilized relative to the cap 10 by tightening the screw 32.

The head of a trial femoral prosthesis is then introduced into the cup, equipped with its trial insert, and the mobility of the hip is tested.

If the hip is stable, the chosen orientation is retained.

If the hip is unstable, the operation of orienting the acetabulum is recommenced.

Upon completion of these operations, the orientation of the joint is determined definitively.

It is then possible to remove the trial insert 33 from the cup and to replace it with a final insert 38 with dimensions identical to those of the trial insert 33 but without any central orifice.

In the cup 16, the final insert takes up the exact place which the trial insert 33 occupied.

Of course, before putting the final insert into place, the cup 16 is fixed in the acetabular cavity with the aid of screws (not shown) which are engaged in the peripheral holes 18.

It is also possible to remove the assembly and put a normal acetabulum into place.

Once this operation has been carried out, it is then possible to place the head of the femoral prosthesis in the acetabulum and to find the correct orientation of the joint thus restored.

The various metal parts constituting the implantable acetabulum according to the invention can be made of titanium, stainless steel, chromium-cobalt or any other biocompatible metal.

It will thus be appreciated that by virtue of what has been described above it is possible to adjust the orientation of the prosthetic acetabulum and to test the mobility of the hip using the trial femoral components, without the choice of position of the acetabulum being definitive.

What is claimed is:

1. A trial acetabulum or implantable acetabulum comprising:

a hemispherical cup intended to be placed in an acetabular cavity;

a hemispherical insert of biocompatible plastic intended to be engaged concentrically in said cup;

an external cap in the form of a spherical dish provided with pins for anchoring in the bone of the acetabular cavity and intended to receive the cup;

an internal plate intended to be placed in the cup opposite the external cap; and connection means for connecting the external cap and the internal plate;

the cap and the plate defining means for adjusting the angular position of the cup in the acetabular cavity as a function of the orientation to be given to the joint;

the connection means for connecting the external cap to the internal plate including means for immobilizing the cup relative to the external cap after the angular position of said cup has been adjusted.

2. The trial acetabulum or implantable acetabulum according to claim 1, wherein the external cap includes:

a threaded centering sleeve, which protrudes inward and is intended to cooperate with an external centering collar provided on the internal plate;

the sleeve and the collar guiding the translational movement of the internal plate relative to the external cap;

a tightening screw having a frustoconical head and intended to be engaged in the threaded sleeve of the external cap;

said frustoconical head cooperating with a seat of corresponding shape formed in the internal plate and coaxial to said collar; and the screw, the threaded sleeve of the external cap, and the collar of the internal plate constituting said connecting means for connecting the cap to the plate.

3. The trial acetabulum or implantable acetabulum according to claim 2, wherein the hemispherical cup includes a central orifice traversed by the screw connecting the external cap to the internal plate, with a clearance which allows the angular position of the cup to be adjusted relative to the cap in all directions.

4. The trial acetabulum or implantable acetabulum according to claim 2, wherein the hemispherical insert is a trial insert which includes a central orifice for access to the screw for connecting the external cap to the internal plate.

5. The trial acetabulum or implantable acetabulum according to claim 2, wherein the insert is a complete and final hemispherical insert which can replace a trial insert upon completion of the operation of orienting and immobilizing the cup relative to the external cap.

6. The trial acetabulum or implantable acetabulum according to claim 5, wherein the head of the screw has a concave end surface, while the summit of the final hemispherical insert has a recess which is intended to prevent the summit of said final hemispherical insert from abutting against the head of the screw.

7. The trial acetabulum or implantable acetabulum according to claim 1, wherein the cup comprises an external zone of reduced thickness for receiving the external cap in such a way as to present, together with the external cap, an almost continuous external surface.

8. The trial acetabulum or implantable acetabulum according to claim 7, wherein the cup has, in its internal wall, a thinned wall portion receiving the internal plate.

9. The trial acetabulum or implantable acetabulum according to claim 8, wherein an angular extent of the external zone receiving the external cap and an angular extent of the internal wall portion receiving the internal plate are greater than angular extents of the cap and of the plate.

\* \* \* \* \*